US009983181B2

(12) United States Patent
Maguire et al.

(10) Patent No.: US 9,983,181 B2
(45) Date of Patent: May 29, 2018

(54) PERSONALIZED CAPNOGRAPHY

(71) Applicant: ORIDION MEDICAL 1987 LTD., Jerusalem (IL)

(72) Inventors: Seamus Maguire, Athlone (IE); Moshe Mandelbaum, Psagot (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 948 days.

(21) Appl. No.: 14/267,524

(22) Filed: May 1, 2014

(65) Prior Publication Data

US 2015/0316520 A1 Nov. 5, 2015

(51) Int. Cl.
*G01N 33/00* (2006.01)
*A61B 5/08* (2006.01)
*G01N 33/497* (2006.01)
*A61B 5/00* (2006.01)
*A61B 5/083* (2006.01)

(52) U.S. Cl.
CPC ........... *G01N 33/004* (2013.01); *A61B 5/082* (2013.01); *A61B 5/0816* (2013.01); *A61B 5/0836* (2013.01); *A61B 5/746* (2013.01); *G01N 33/497* (2013.01)

(58) Field of Classification Search
CPC .. G01N 33/004; G01N 33/497; A61B 5/0836; A61B 5/746; A61B 5/0816; A61B 5/082
See application file for complete search history.

(56) References Cited

U.S. PATENT DOCUMENTS

| 6,997,880 | B2 * | 2/2006 | Carlebach | A61B 5/0836 600/311 |
| 2009/0118632 | A1 * | 5/2009 | Goepp | A61B 5/0836 600/532 |
| 2010/0317986 | A1 * | 12/2010 | Colman | A61B 5/0836 600/532 |
| 2012/0266955 | A1 | 10/2012 | Kim | |

* cited by examiner

*Primary Examiner* — Mohamed Charioui
*Assistant Examiner* — Jeremy Delozier

(57) ABSTRACT

Control logic, device and method including same configured to receive a measured carbon dioxide ($CO_2$) related parameter of a patient, to obtain a patient specific baseline for said $CO_2$ related parameter, the patient specific baseline determined based on a characteristic of the patient; to compute a deviation of the measured $CO_2$ related parameter from the patient specific baseline; and to trigger an alarm when the deviation crosses a predetermined threshold value.

7 Claims, 3 Drawing Sheets

PERSONALIZED CAPNOGRAPHY

TECHNICAL FIELD

The present disclosure relates generally to the field of personalized capnography and alarm management.

BACKGROUND

Medical monitoring devices provide crucial data regarding a patient's medical condition. For example capnographs measure and provides values of the carbon dioxide ($CO_2$) concentration in exhaled breath, and as such may be used to characterize patient's ventilation functioning.

The medical devices are often configured to trigger an alarm alerting health care providers that a monitored parameter deviates from a threshold value. For example, a capnograph may set off an alarm when deviations or changes in the patient's $CO_2$ levels are detected.

SUMMARY

Aspects of the disclosure, in some embodiments thereof, relate to personalized configured to interpret $CO_2$ waveforms according to a patient's personal data and medical history. The personalized capnography disclosed herein may facilitate the clinicians to swiftly obtain a refined assessment of a patient's respiratory status. Furthermore, the personalized capnography may also be utilized to reduce the number of false alarms.

Frequent non-actionable alarms are a common complaint of caregivers. These alarms disrupt clinical workflow, are troubling to the patient and his or her surroundings, and may lead to alarm fatigue amongst the medical personnel. As a consequence thereof, true alerts may be overseen, as the alarm is ignored or even turned off, with a possibly tragic outcome.

According to some embodiments, the control logic, disclosed herein, is configured to obtain a measured carbon dioxide ($CO_2$) related parameter(s) of a patient, to obtain a patient specific baseline for the $CO_2$ related parameter(s), the patient specific baseline determined based on a characteristic(s) of the patient, and to compute a deviation of the measured $CO_2$ related parameter(s) from the patient specific baseline $CO_2$.

This may enable to trigger an alarm only when the measured $CO_2$ related parameter(s) deviates from a "personal" baseline rather than an "absolute" baseline common to all patients. Thus, the control logic, disclosed herein enables reducing the amount of both false positive and false negative alarms by personalizing the alarm settings. This may in turn avoid disruption of clinicians' workflow while enhancing the confidence in the remaining alarms, consequently reducing the risk of clinicians discounting true alert.

According to some embodiments, the control logic, disclosed herein, is configured to receive a measured $CO_2$ related parameter(s), to obtain a patient specific first baseline for the $CO_2$ related parameter, the patient specific first baseline determined based on a background variable of the patient, and to obtain a patient specific second baseline for the $CO_2$ related parameter, the patient specific second baseline determined based on the background variable and on a background disease of the patient. The control logic is further configured to compute a first deviation value based on a deviation of the measured $CO_2$ related parameter from the first baseline and to compute a second deviation value based on a deviation of the measured $CO_2$ related parameter from the second baseline.

The control logic may thereby enable the caregiver to rapidly assess to what extent measurements obtained from a patient are anomalous relative to normal subjects sharing the same background variable(s) and relative to subjects sharing the same background variable(s) as well as the same background disease(s).

According to some embodiments, there is provided a control logic configured to receive a measured carbon dioxide ($CO_2$) related parameter of a patient, obtain a patient specific baseline for the $CO_2$ related parameter, the patient specific baseline determined based on a characteristic of the patient; compute a deviation of the measured $CO_2$ related parameter from the patient specific baseline; and trigger an alarm when the deviation crosses a predetermined threshold value.

According to some embodiments, the $CO_2$ related parameter may include end tidal $CO_2$ ($EtCO_2$), respiration rate, waveform shape, waveform scale or any combination thereof. Each possibility is a separate embodiment.

According to some embodiments, the patient characteristic may include age, sex, weight, fitness, background disease or any combination thereof. Each possibility is a separate embodiment.

According to some embodiments, the background disease may include asthma, chronic obstructive pulmonary disease (COPD), broncho-pulmonary dysplasia (BPD) or any combination thereof. Each possibility is a separate embodiment.

According to some embodiments, the $CO_2$ related parameter may include an algorithmically-derived index of multiple $CO_2$ related parameters. According to some embodiments, the algorithmically-derived index of multiple $CO_2$ related parameters is computed by:

(a) characterizing a first measured $CO_2$ related parameter based on a comparison of the first measured $CO_2$ related parameter against a first reference value;

(b) characterizing a second measured $CO_2$ related parameter based on a comparison of the second measured $CO_2$ related parameter against a second reference value; and (c) computing the index value based on values associated with each of the characterized first and second measured $CO_2$ related parameters.

According to some embodiments, the patient specific baseline is a $CO_2$ related parameter obtained from said patient prior to a medical procedure. According to some embodiments, the patient specific baseline is a $CO_2$ related parameter representative of patients having the same patient characteristic. According to some embodiments, the representative $CO_2$ related parameter is provided to said control logic through a user interphase.

According to some embodiments, the control logic may be configured to up-load the patient specific baseline carbon dioxide ($CO_2$) related parameter and the measured carbon dioxide ($CO_2$) related parameter to a remote database. According to some embodiments, the database may be continuously up-loaded. According to some embodiments, the database may be configured to compute an integrated data-set (e.g. an integrated patient specific baseline carbon dioxide ($CO_2$) related parameter) specific to patients having the same background characteristics (e.g. suffering from a particular background disease).

According to some embodiments, there is provided a control logic configured to receive a measured $CO_2$ related parameter from a patient; to obtain a patient specific first baseline for the $CO_2$ related parameter, the patient specific first baseline determined based on a background variable of the patient; to obtain a patient specific second baseline for the $CO_2$ related parameter, the patient specific second baseline determined based on the background variable and on a background disease of the patient; to compute a first deviation value based on a deviation of the measured $CO_2$ related parameter from the first baseline; and to compute a second deviation value based on a deviation of the measured $CO_2$ related parameter from the second baseline.

According to some embodiments, the control logic may be configured to display the first and second deviation values.

According to some embodiments, the control logic may be configured to trigger an alarm when the second deviation crosses a predetermined threshold value. According to some embodiments, the control logic may be configured to trigger an alert when the first deviation crosses a predetermined threshold value.

According to some embodiments, the $CO_2$ related parameter may include end tidal $CO_2$ ($EtCO_2$), respiration rate, waveform shape, waveform scale or any combination thereof. Each possibility is a separate embodiment.

According to some embodiments, the background variable may include age, sex, weight, fitness or any combination thereof. Each possibility is a separate embodiment.

According to some embodiments, the background disease may include asthma, chronic obstructive pulmonary disease (COPD), broncho-pulmonary dysplasia (BPD) or any combination thereof. Each possibility is a separate embodiment.

According to some embodiments, the $CO_2$ related parameter may include an algorithmically-derived index of multiple $CO_2$ related parameters. According to some embodiments, the algorithmically-derived index of multiple $CO_2$ related parameters is computed by:

(a) characterizing a first measured $CO_2$ related parameter based on a comparison of the first measured $CO_2$ related parameter against a first reference value;

(b) characterizing a second measured $CO_2$ related parameter based on a comparison of the second measured $CO_2$ related parameter against a second reference value; and (c) computing the index value based on values associated with each of the characterized first and second measured $CO_2$ related parameters.

According to some embodiments, the control logic may be configured to up-load the patient specific baseline carbon dioxide ($CO_2$) related parameter and the measured carbon dioxide ($CO_2$) related parameter to a remote database. According to some embodiments, the database may be continuously up-loaded. According to some embodiments, the database may be configured to compute an integrated data-set (e.g. an integrated patient specific baseline carbon dioxide ($CO_2$) related parameter) specific to patients having the same background characteristics (e.g. suffering from a particular background disease).

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments of the disclosure may be practiced. The figures are for the purpose of illustrative discussion and no attempt is made to show structural details of an embodiment in more detail than is necessary for a fundamental understanding of the teachings of the disclosure.

DETAILED DESCRIPTION

Figure 1:
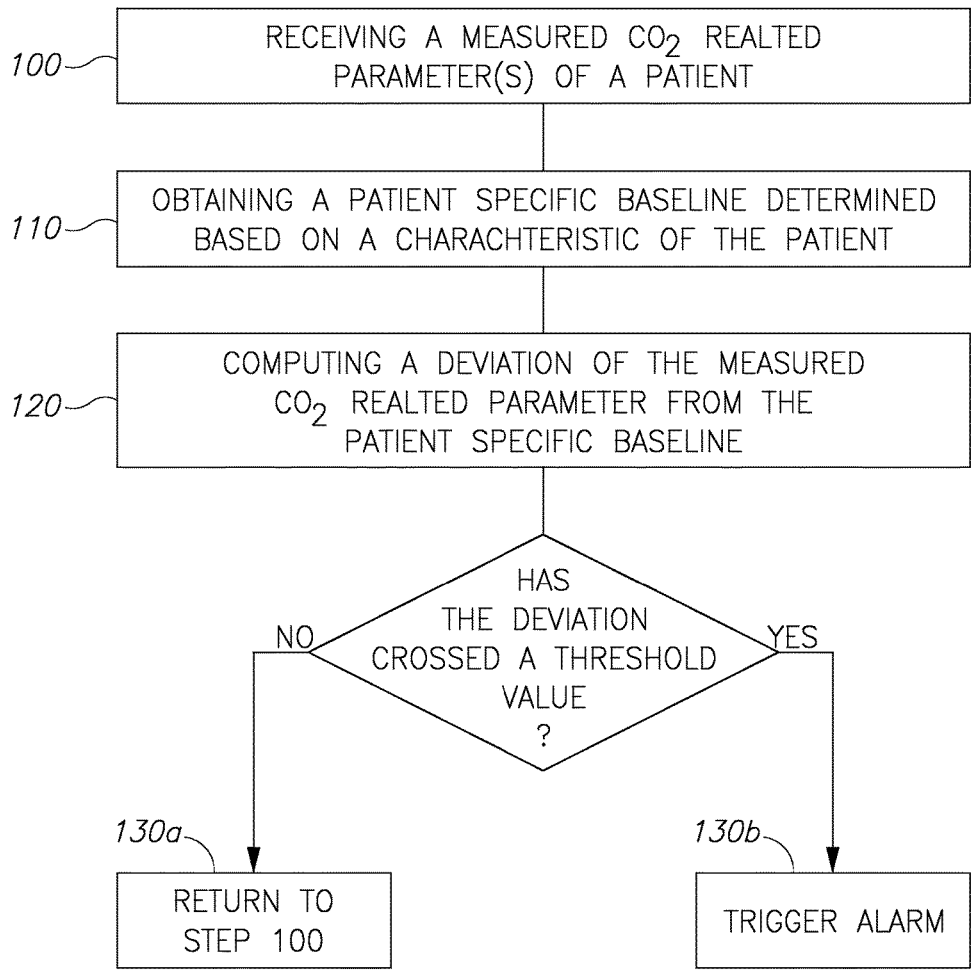
FIG. 1 is an illustrative flowchart of the operation of a control logic, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

The present disclosure relates generally to the field of personalized capnography and alarm management.

There is provided, according to some embodiments, a control logic configured to receive a measured carbon dioxide ($CO_2$) related parameter of a patient, and to obtain a patient specific baseline for the $CO_2$ related parameter, the patient specific baseline determined based on a characteristic of the patient. The control logic may then compute a deviation of the measured $CO_2$ related parameter from the patient specific baseline; and trigger an alarm if the deviation crosses a predetermined threshold value.

As referred to herein, the terms "patient" and "subject" may interchangeably be used and may relate to a subject being monitored by a capnograph or any other device configured to monitor $CO_2$ related parameters.

As used herein, the terms "clinician" and "caregiver" may be interchangeably used and may refer to any medical personnel involved in the care of the patient.

According to some embodiments, the terms "characteristic", "variable" and "data" may be used interchangeably and may refer to any attribute of the subject which may influence $CO_2$ related parameter readings. According to some embodiments, the term "characteristic" may be a broader term and may include the term "variable". According to some embodiments, patient variables may include, but are not limited to, age, sex, weight, fitness or any combination thereof. Each possibility is a separate embodiment. According to some embodiments, patient characteristics may include, but are not limited to age, sex, weight, fitness, background disease or any combination thereof. Each possibility is a separate embodiment. According to some embodiments exemplary background diseases include asthma, chronic obstructive pulmonary disease (COPD), broncho-pulmonary dysplasia (BPD), hyperventilation, hypoventilation or any combination thereof. Each possibility is a separate embodiment.

As used herein, the term "measured carbon dioxide ($CO_2$) related parameter" may refer to parameters obtained from capnograph readings. According to some embodiments, the parameters may be continuously obtained from the capnograph.

As used herein, the term "patient specific baseline" may refer to a parameter(s) serving as a reference point(s) to the measured $CO_2$ related parameters. According to some embodiments, the patient specific baseline may refer to baseline parameters incorporating and/or taking into consideration the characteristics of the patient. According to some embodiments, the baseline $CO_2$ related parameter is a $CO_2$ related parameter obtained from the (same) patient for example prior to a medical procedure. Exemplary medical procedures, typically requiring $CO_2$ monitoring, include sedation and surgery, but other procedures for which capnographic monitoring is recommended are also applicable. According to some embodiments, the baseline $CO_2$ related parameter is a $CO_2$ related parameter obtained from patients having the same patient characteristic(s). According to some embodiments, the baseline $CO_2$ related parameter may refer to data obtained from patients having the same patient characteristic(s) and stored by a computer memory for example, but not limited to, the control logic. According to some embodiments, the baseline $CO_2$ related parameter may refer to theoretical (textbook) data of waveforms representative of patients having the same patient characteristic(s).

According to some embodiments, the control logic may be configured to transfer and/or upload the baseline $CO_2$ related parameter and/or the measured carbon dioxide ($CO_2$) related parameter to a computer memory, for example, but not limited to a remote database or a centralized system. According to some embodiments, the up-loaded data may then be downloaded to calculate deviation values. According to some embodiments, the up-load may be continuous, semi-continuous, at predefined time points (e.g. every 5 min) or event oriented (e.g. every time an alert/alarm is triggered). It is thus understood by one of ordinary skill in the art that the database may be revised in an ongoing manner. According to some embodiments, a learning algorithm may be applied to the stored data in order to further refine and/or personalize the data set and in effect the parameters calculated therefrom.

According to some embodiments, the control logic may be further configured to produce an integrated data-set specific to patients having the same background characteristics (e.g. suffering from a particular background disease), based on up-loaded baseline $CO_2$ related parameters and/or measured carbon dioxide ($CO_2$) related parameters from each of the "similar" patients.

According to some embodiments, the stored data may be configured to capture the patient(s)'s response to a treatment (e.g. adjustment of ventilation machine settings), and thereby enable an improved and personalized evaluation of treatment efficiency. Moreover, the control logic may be configured to produce a treatment recommendation, such as, but not limited to, deciding on ventilation settings based on the up-loaded personal data-set.

It is understood by one of ordinary skill in the art that since the patient specific baseline differs among patients due to their different personal characteristics, the control logic enables to personalize alarm settings thereby reducing the amount of both false positive and false negative alarms.

According to some embodiments, the patient specific baseline may be retrieved by the control logic upon providing the patient characteristic(s) to the control logic. For example, the clinician may provide the patient characteristic(s) to the control logic through a user interface. According to some embodiments, the patient characteristic(s) may be encoded at the time of patient enrolment. According to some embodiments, the medical history including some or part of the patient's characteristics may be retrieved from a medical file of the patient.

According to some embodiments, the $CO_2$ related parameter may include end tidal $CO_2$ ($EtCO_2$), respiration rate, waveform shape, waveform scale or combinations thereof. Each possibility is a separate embodiment.

According to some embodiments "shape factors", as used herein, may characterize and/or describe the shape or pattern of a $CO_2$ waveform. A shape factor may include, for example, parameters of a non-linear function describing an upstroke of the waveform. The shape factors of the waveform are generally indicative of physiological condition(s) of a patient. For example, dominant shape factors of the waveform(s) may relate to respiratory processes such as the mechanics of breathing. Shape factors may be a parameter(s) of a function or a set(s) of binary values (in the form of a vector or a matrix). It is understood to one of ordinary skill in the art, that different respiratory conditions may influence the shape of the waveform, and thus the shape factors used to describe the waveform. As a non-limiting example, the upstroke of the $CO_2$ waveform may be prolonged (slope decreased) in patients suffering from respiratory disorders such as COPD.

According to some embodiments, "scale factors", as used herein, may be the waveform values and/or ratios, for example, height, width, width at half-height, duty cycle, inhalation to exhalation ratio (I to E ratio) or any other value or combination of values. Scale factor features typically relate to general processes and/or body functions, such as, perfusion, shunt, metabolism, ventilation, respiration and the like. It is understood to one of ordinary skill in the art, that different respiratory conditions may influence the scale factors used to describe the waveform. As a non-limiting example, the height of the $CO_2$ waveform may be decreased ($EtCO_2$ decreased) in patients suffering from respiratory obstruction, such as for example asthma.

According to some embodiments, the term "a" may refer to at least one. According to some embodiments, the term "at least one" may refer to 1, 2, 3, 4, 5, or more parameters. Each possibility is a separate embodiment. For example, with regards to $CO_2$ related parameters, the $CO_2$ related parameters (measured and baseline) may be $EtCO_2$ and respiration rate (RR). Accordingly, the control logic may compute a delta $EtCO_2$ value—the deviation between the measured $EtCO_2$ and the baseline $EtCO_2$; and a delta RR—the deviation between the measured RR and the baseline RR.

According to some embodiments, the control logic may compute the deviation by simple subtraction of the measured $CO_2$ related parameter (e.g. measured RR) from the patient specific baseline (e.g. baseline RR).

According to some embodiments, the control logic may compute the deviation by performing statistical analysis of the deviation over a predetermined period of time. It is understood by one of ordinary skill in the art that that monitoring devices, such as for example capnographs, may continuously monitor breath samples and thus continuously provide measurements of the $CO_2$ related parameter(s) to the control logic. In effect, the deviation may be calculated based on a statistical analysis of n number of measurements obtained during a predetermined period of time for example y seconds. It is further understood that the measured $CO_2$ related parameter may be continuously updated (moving average) such that each measured $CO_2$ related parameter provided to the control logic may represent n number of measurements obtained during a measurement window of y seconds and updated every z seconds. According to some embodiment, the measured $CO_2$ related parameter provided to the control logic may represent 0.5-100 measurements. According to some embodiment, the measured $CO_2$ related parameter provided to the control logic may represent 2-50 measurements. According to some embodiment, the measured $CO_2$ related parameter provided to the control logic may represent 5-25 measurements.

According to some embodiments, the $CO_2$ related parameter may include an algorithmically-derived index of multiple $CO_2$ related parameters. According to some embodiments, the algorithmically-derived index of multiple $CO_2$ related parameters may be computed by:

(a) characterizing a first measured $CO_2$ related parameter based on a comparison of the first measured $CO_2$ related parameter against a first reference value;

(b) characterizing a second measured $CO_2$ related parameter based on a comparison of the second measured $CO_2$ related parameter against a second reference value; and (c) computing the index value based on values associated with each of the characterized first and second measured $CO_2$ related parameters.

As used herein, the term "alarm" may refer to an audible alarm configured to alert the clinician. According to some embodiments, the clinician may be required to approach the patient in order to turn the alarm off.

As used herein, the terms "alert" and "warning" may be interchangeably used and may refer to a signal provided to a clinician, but which do not require his or hers immediate attention. According to some embodiments, the clinician may not be required to approach the patient in order to turn off the alert. As a non-limiting example, the alert may be an audible signal provided to a clinician (for example through a personal communication device such as, but not limited to a beeper or a smart phone). According to some embodiments, the alert may be stored in the medical history of the patient for further use by caregivers.

According to some embodiments, the at least one $CO_2$ related parameter is user selectable. It is understood by one of ordinary skill in the art that different medical parameters may be measured for different medical conditions.

According to some embodiments, the control logic is configured to store data including, but not limited to, the at least one measured $CO_2$ related parameter, the patient specific baseline, the deviation of the at least one measured $CO_2$ related parameter from the patient specific baseline, alerts, alarms or any combination thereof. Each possibility is a separate embodiment.

According to some embodiments, the data, or parts thereof, may be reported to the clinician. According to some embodiments, the reported data may serve as a tool in the assessment of the patient's condition.

According to some embodiments, there is provided a control logic configured to: receive a measured $CO_2$ related parameter from a patient, to obtain a patient specific first baseline for the $CO_2$ related parameter, the patient specific first baseline determined based on a background variable of said patient, and to compute a first deviation value based on a deviation of the measured $CO_2$ related parameter from the first baseline. The control logic may be further configured to obtain a patient specific second baseline for the $CO_2$ related parameter, the patient specific second baseline determined based on the background variable and on a background disease of the patient, and to compute a second deviation value based on a deviation of the measured $CO_2$ related parameter from the second baseline.

According to some embodiments, the control logic may display the first and second deviation values. This may enable the caregiver to rapidly assess to what extent measurement obtained for a patient are anomalous relative to normal subjects sharing the same background variable and relative to subjects sharing the same background variable as well as the same background disease.

According to some embodiments, the control logic may compare the first deviation value to a predetermined first threshold value and the second deviation to a predetermined second threshold value. It is understood by one of ordinary skill in the art the first threshold vale may be the same or different from the second threshold value.

According to some embodiments, the control logic may trigger an alarm when the second deviation value crosses a (second) predetermined threshold value. It is understood by one of ordinary skill in the art that this may serve to reduce the amount of actionable alarms as the alarm is triggered only when the measurements obtained are anomalous to patients suffering from the same background diseases and sharing the same background variable. According to some embodiments, the control logic may trigger an alert when the first deviation value crosses a (first) predetermined threshold value. As detailed above, the alert may not require the clinician's immediate attention, but may provide an indication to the clinician that the measurements obtained from the patient are abnormal as compared to healthy subjects having the same background variable. The alert may be an audible signal distinct from the traditional alarm in order to enable the clinician to distinguish between action requiring alarms and non-actionable alerts. According to some embodiments, the alert may be stored in the medical history of the patient (along with alarms) thereby assisting the clinician in assessing the patients respiratory status.

It is understood that the deviation required to trigger the alarm may be the same or different from the deviation required to trigger the alert. It is further understood that since the alarm settings have been personalized, the deviations required to trigger the alarm may be less than the deviation required to trigger a traditional alarm. Advantageously, the more strict deviation requirements may not elevate the number of triggered alarms, due to the personalized baseline settings.

According to some embodiments, the $CO_2$ related parameter may include end tidal $CO_2$ ($EtCO_2$), respiration rate, waveform shape, waveform scale or any combination thereof. Each possibility is a separate embodiment.

According to some embodiments, the background variable may include age, weight, sex, fitness or any combination thereof. Each possibility is a separate embodiment. It is understood by one of ordinary skill in the art that waveforms obtained from patients suffering from a background disease may deviate from normal waveforms in a manner dependent on the patient's variable(s). As a non-limiting example, a normal weight patient suffering from asthma may have a waveform closer to a 'normal' waveform than a patient being both overweight and suffering from asthma.

According to some embodiments, the background diseases may include asthma, chronic obstructive pulmonary disease (COPD), broncho-pulmonary dysplasia (BPD) or combinations thereof. According to some embodiments, the background disease may include hyper- and hypo ventilation. According to some embodiments, the background disease provided to the control logic is 'no background disease'.

According to some embodiments, the $CO_2$ related parameter may include an algorithmically-derived index of multiple $CO_2$ related parameters. According to some embodiments, the algorithmically-derived index of multiple $CO_2$ related parameters may be computed by:

(a) characterizing a first measured $CO_2$ related parameter based on a comparison of the first measured $CO_2$ related parameter against a first reference value;

(b) characterizing a second measured $CO_2$ related parameter based on a comparison of the second measured $CO_2$ related parameter against a second reference value; and (c) computing the index value based on values associated with each of the characterized first and second measured $CO_2$ related parameters.

According to some embodiments, the first and/or second baselines may be retrieved by the control logic upon providing the background variable and the background disease to the control logic. Hence, the clinician may provide the patient background variable (s) and background disease(s) to the control logic for example through a user interface. According to some embodiments, the background variable may be encoded at the time of enrolling the patient. According to some embodiments, the medical history and and/or background variable may be retrieved from a medical file of the patient.

According to some embodiments, there is provided a medical device including a control logic configured to receive a measured carbon dioxide ($CO_2$) related parameter of a patient, and to obtain a patient specific baseline for the $CO_2$ related parameter, the patient specific baseline determined based on a characteristic of the patient. The control logic may then compute a deviation of the measured $CO_2$ related parameter from the patient specific baseline; and trigger an alarm if the deviation crosses a predetermined threshold value.

According to some embodiments, there is provided a medical device including a control logic configured receive a measured $CO_2$ related parameter from a patient, to obtain a patient specific first baseline for the $CO_2$ related parameter, the patient specific first baseline determined based on a background variable of said patient, and to compute a first deviation value based on a deviation of the measured $CO_2$ related parameter from the first baseline. The control logic may be further configured to obtain a patient specific second baseline for the $CO_2$ related parameter, the patient specific second baseline determined based on the background variable and on a background disease of the patient, and to compute a second deviation value based on a deviation of the measured $CO_2$ related parameter from the second baseline.

According to some embodiments, the medical device may be a capnograph.

According to some embodiments, the medical device includes at least one sensor. According to some embodiments, the at least one sensor is a $CO_2$ sensor, a flow sensor, an infra-red (IR) sensor or combinations thereof. According to some embodiments, the term "at least one" when referring to a sensor may include 1, 2, 3, 4, 5 or more sensors. Each possibility is a separate embodiment.

According to some embodiments, there is provided a method for reducing non-actionable alarms. According to some embodiments the method may include receiving a measured carbon dioxide ($CO_2$) related parameter of a patient, obtaining a patient specific baseline for the $CO_2$ related parameter, the patient specific baseline determined based on a characteristic of the patient, computing a deviation of the measured $CO_2$ related parameter from the patient specific baseline, and triggering an alarm if the deviation crosses a predetermined threshold value According to some embodiments, the method may also include determining which medical parameters will be measured for example based on the medical record of the patient. According to some embodiments, the at least one measured medical parameter may include end tidal $CO_2$ ($EtCO_2$), respiration rate, waveform shape, waveform scale or any combination thereof. Each possibility is a separate embodiment.

According to some embodiments, the method may further include storing data, such as the measured $CO_2$ related parameter, the patient specific baseline, the deviation of the measured $CO_2$ related parameter from the patient specific baseline, alerts, alarms or any combination thereof. Each possibility is a separate embodiment.

According to some embodiments, there is provided a method for personalizing capnography, the method including receiving a measured $CO_2$ related parameter from a patient, obtaining a patient specific first baseline for the $CO_2$ related parameter, the patient specific first baseline determined based on a background variable of the patient, and to compute a first deviation value based on a deviation of the measured $CO_2$ related parameter from the first baseline. The method may further include obtaining a patient specific second baseline for the $CO_2$ related parameter, the patient specific second baseline determined based on the background variable and on a background disease of the patient, and to compute a second deviation value based on a deviation of the measured $CO_2$ related parameter from the second baseline.

According to some embodiments, the method includes displaying the first and/or second deviation values.

According to some embodiment, the method includes triggering an alarm when the second deviation value crosses a predetermined threshold value. According to some embodiments, the method includes triggering an alert when the first deviation value crosses a predetermined threshold value.

According to some embodiments, the method may include determining which medical parameters will be measured for example based on the medical record of the patient. According to some embodiments, the at least one measured medical parameter may include end tidal $CO_2$ ($EtCO_2$), respiration rate, waveform shape, waveform scale or any combination thereof. Each possibility is a separate embodiment.

According to some embodiments, the method may include storing data, such as the measured $CO_2$ related parameter, the patient specific baseline, the deviation of the measured $CO_2$ related parameter from the patient specific baseline, alerts, alarms or any combination thereof. Each possibility is a separate embodiment.

Before explaining at least one embodiment in detail, it is to be understood that aspects of the embodiments are not necessarily limited in their application to the details of construction and the arrangement of the components and/or methods set forth herein. Some embodiments may be practiced or carried out in various ways. The phraseology and terminology employed herein are for descriptive purpose and should not be regarded as limiting.

Reference is now made to FIG. 1 which is an illustrative flowchart of the operation of a control logic, according to some embodiments. At step 100, the control logic receives a measured carbon dioxide ($CO_2$) related parameter(s) of a patient having certain patient characteristic(s). At step 110, the control logic obtains a patient specific baseline for the $CO_2$ related parameter, the patient specific baseline determined based on the same patient characteristic(s). At step 120, the control logic computes a deviation of the measured $CO_2$ related parameter(s) from a patient specific baseline.

Does the deviation cross a predetermined threshold value, the control logic triggers an alarm, in step 130b. Otherwise, the control logic returns to step 100 if the threshold value has not been crossed, as described in step 130a.

Figure 2:
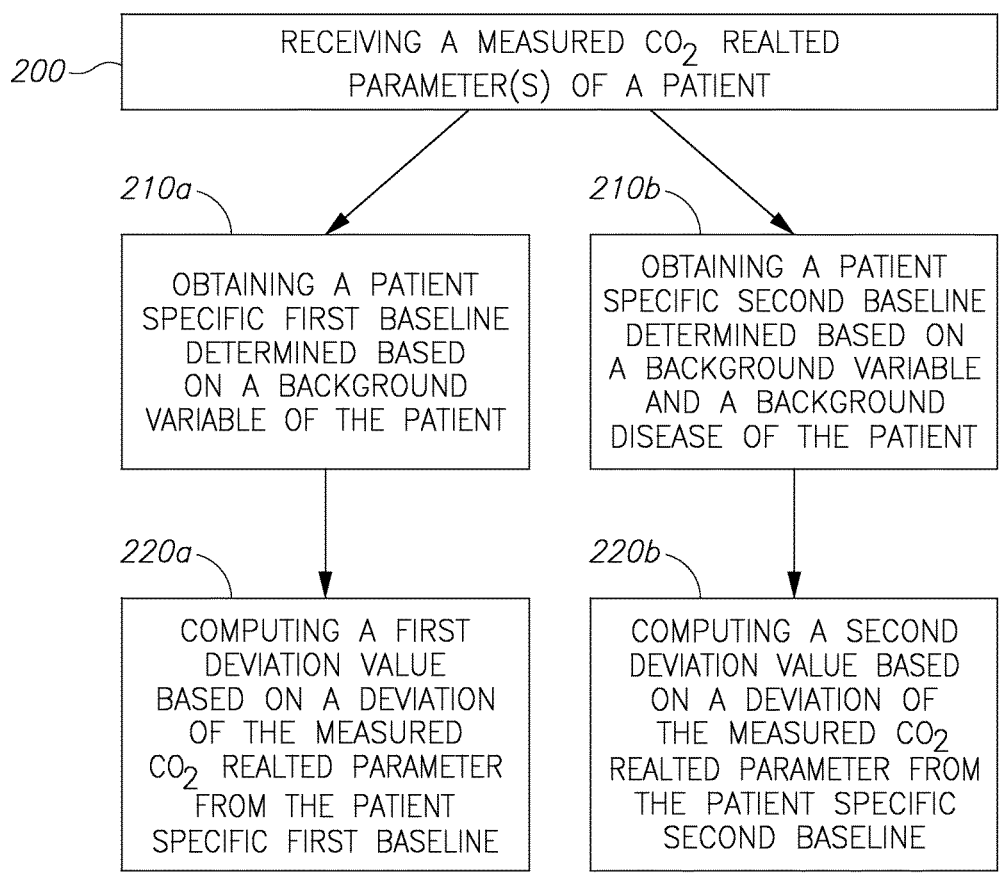
FIG. 2 is an illustrative flowchart of the operation of a control logic, according to some embodiments.

Reference is now made to FIG. 2 which is an illustrative flowchart of the operation of a control logic, according to some embodiments. At step 200, the control logic receives a measured carbon dioxide ($CO_2$) related parameter(s) of a patient determined as having certain background variable(s) and optionally background disease(s). At step 210a, the control logic obtains a patient specific first baseline for the $CO_2$ related parameter, the patient specific first baseline determined based on the (same) background variable(s) of the patient. At step 210b, the control logic obtains a patient specific second baseline for the $CO_2$ related parameter, the patient specific second baseline determined based on the (same) characteristic(s) and background disease(s) of the patient. At step 220a and 220b, the control logic computes a first and a second deviation value, respectively, based on a deviation of the measured $CO_2$ related parameter(s) from the obtained first and second baselines.

Figure 3:
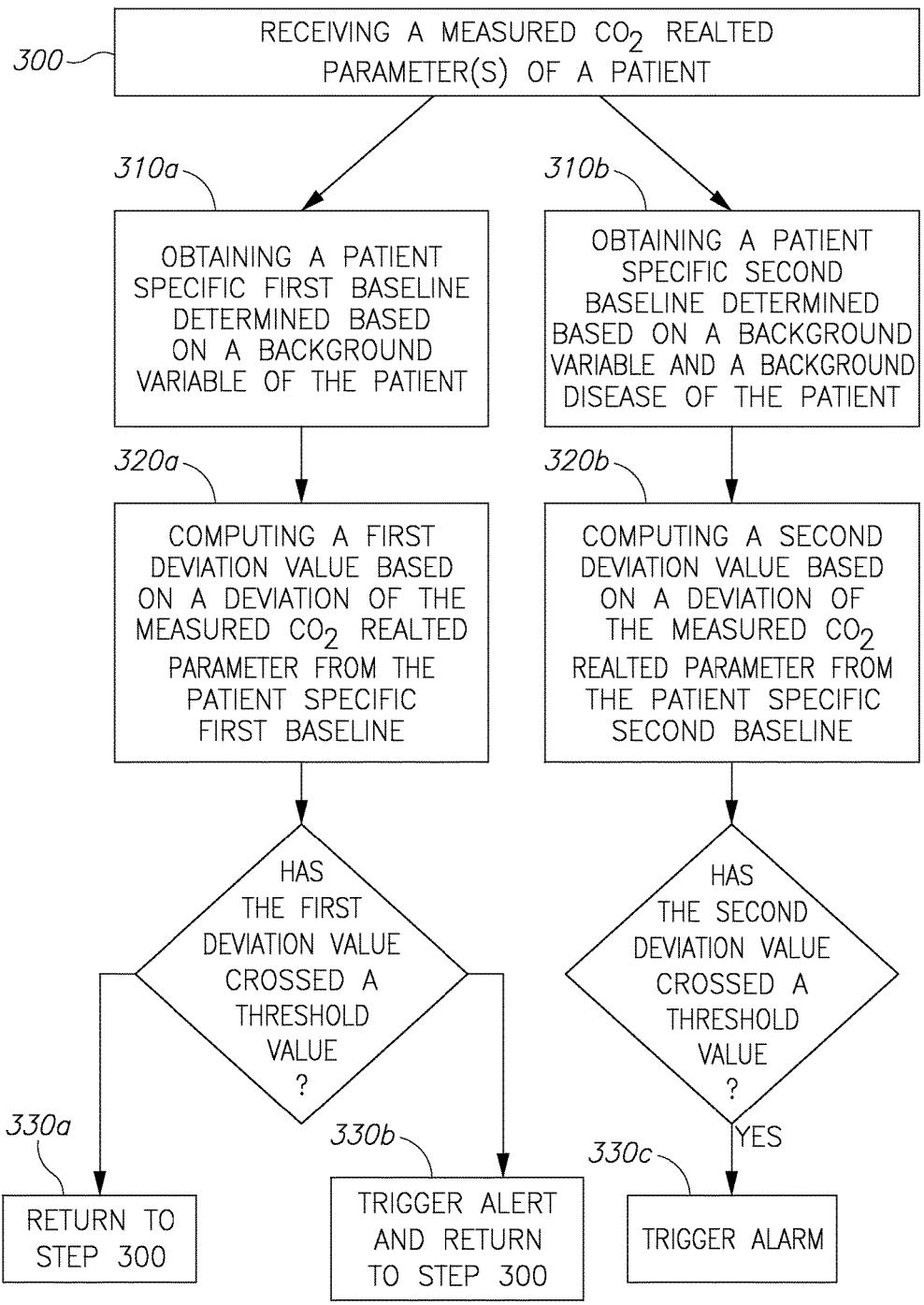
FIG. 3 is an illustrative flowchart of the operation of a control logic, according to some embodiments.

Reference is now made to FIG. 3 which is an illustrative flowchart of the operation of a control logic, according to some embodiments. At step 300, the control logic receives a measured carbon dioxide ($CO_2$) related parameter(s) of a patient determined as having certain background variable(s) and optionally background disease(s). At step 310a, the control logic obtains a patient specific first baseline for the $CO_2$ related parameter, the patient specific first baseline determined based on the (same) background variable(s) of the patient. At step 310b, the control logic obtains a patient specific second baseline for the $CO_2$ related parameter, the patient specific second baseline determined based on the (same) characteristic(s) and background disease(s) of the patient. At step 320a, the control logic computes a first deviation value based on a deviation of the measured $CO_2$ related parameter(s) from the obtained first baseline. Has the first threshold value been crossed, the control logic triggers an alert, as in step 330b. Otherwise, if the first threshold value has not been crossed, the control logic returns to step 300, as described in step 330a. Similarly, at step 320b, the control logic computes a second deviation value based on a deviation of the measured $CO_2$ related parameter(s) from the obtained second baseline. Has the second threshold value been crossed, the control logic triggers an alarm, as described in step 330c. It is understood to one of ordinary skill in the art, that steps 320a, and 320b (and subsequent steps 330a/b and 330c) may be performed simultaneously. Alternatively, step 320a may be performed in a sequential manner (prior to or after) steps 320b.

It is further understood that variations may occur in the operation of the control logic and that numerous cycles of operation is inherent to the operation of the logic although a single operation cycle is also optional.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

What is claimed is:

1. A patient monitor system comprising control logic configured to:
   receive a first measured carbon dioxide ($CO_2$) related parameter of a patient measured by a $CO_2$ sensor of a capnography;
   determine a first patient baseline for the first measured $CO_2$ related parameter, wherein the first patient baseline is a first personalized baseline that is specific to the patient and is determined based on a characteristic of the patient;
   determine a first deviation of the first measured $CO_2$ related parameter based on a relationship between the first measured $CO_2$ related parameter and the first patient baseline;
   receive a second measured $CO_2$ related parameter of the patient measured by the $CO_2$ sensor of the capnography positioned on the patient;
   determine a second patient baseline for the second measured $CO_2$ related parameter, wherein the second patient baseline is a second personalized baseline that is specific to the patient and is determined based on a health condition of the patient;
   determine a second deviation of the second measured $CO_2$ related parameter based on a relationship between the second measured $CO_2$ related parameter and the second patient baseline;
   determine a respiratory condition of the patient based on the first and second deviations;
   trigger an alert associated with an abnormal measured $CO_2$ related parameter in response to the first deviation crossing a first predetermined threshold value;
   trigger an alarm associated with the respiratory condition of the patient in response to the second deviation crossing a second predetermined threshold value; and
   monitor the respiratory condition of the patient based at least in part on the triggered alert and the triggered alarm.

2. The patient monitor system of claim 1, wherein the first measured $CO_2$ related parameter comprises: end tidal $CO_2$ ($EtCO_2$), respiration rate, waveform shape, waveform scale or any combination thereof.

3. The patient monitor system of claim 1, wherein the patient characteristic comprises age, sex, weight, fitness, background disease or any combination thereof.

4. The patient monitor system of claim 1, wherein the background disease comprises asthma, chronic obstructive pulmonary disease (COPD), broncho-pulmonary dysplasia (BPD) or any combination thereof.

5. The patient monitor system of claim 1, wherein the alert and the alarm are different audible signals.

6. The patient monitor system of claim 1, wherein the computer logic is configured to output a treatment recommendation based on the first measured $CO_2$ related parameter, the second measured $CO_2$ related parameter, the first patient baseline, the second patient baseline, or a combination thereof.

7. The patient monitor system of claim 1, comprising a display, and wherein the computer logic is configured to display the first measured $CO_2$ related parameter, the second measured $CO_2$ related parameter, the first deviation, the second deviation, or a combination thereof on the display.

* * * * *